United States Patent [19]

Alicot

[11] Patent Number: 4,628,103

[45] Date of Patent: Dec. 9, 1986

[54] PROCESS FOR THE PREPARATION OF 3-AMINO-1,2,4-TRIAZOLE

[75] Inventor: Michel Alicot, La Barthe de Neste, France

[73] Assignee: Atochem, France

[21] Appl. No.: 746,287

[22] Filed: Jun. 19, 1985

[30] Foreign Application Priority Data

Jun. 20, 1984 [FR] France ................. 84 09663

[51] Int. Cl.$^4$ ......................... C07D 249/14
[52] U.S. Cl. ................................. 548/266
[58] Field of Search ........................ 548/266

[56] References Cited

FOREIGN PATENT DOCUMENTS 1300971 7/1962 France ................. 548/266
47-8820 3/1972 Japan ................. 548/266

*Primary Examiner*—Robert T. Bond
*Attorney, Agent, or Firm*—Brooks, Haidt, Haffner & Delahunty

[57] ABSTRACT

A process for preparing 3-amino-1,2,4-triazole by reacting hydrazine hydrate, cyanamide and formic acid to form aminoguanidine formate and cyclizing the formate, wherein hydrazine hydrate and formic acid are simultaneously added to the cyanamide at 0° to 10° C. and a pH of 6 to 7, maintaining the mixture at 60° to 100° C. and a pH of 7 to 8 to form aminoguanidine formate, evaporating the aminoguanidine formate solution at 30° to 60° C. to a solids content of 100 to 700 g/L, filtering and washing the formate to a dicyandiamide content below 0.25%, and heating the formate at 110° to 200° C. to obtain the aminotriazole.

10 Claims, No Drawings

PROCESS FOR THE PREPARATION OF 3-AMINO-1,2,4-TRIAZOLE

BACKGROUND OF THE INVENTION

The present invention relates to the synthesis of 3-amino-1,2,4-triazole, and more particularly, it relates to a method for synthesizing this aminotriazole in a purer form and with improved yields.

3-Amino-1,2,4-triazole has the formula:

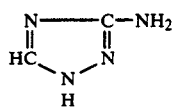

and is employed chiefly as weedkiller and, to a lesser extent, as a starting material for chemical syntheses (more particularly in the dye industry).

Commercially, 3-amino-1,2,4-triazole is obtained by reacting an aminoguanidine salt (usually the bicarbonate) with formic acid, followed by cyclization of the aminoguanidine formate so produced, as shown in U.S. Pat. No. 2,875,209. In the initial stage, the aminoguanidine is obtained in the form of a water-soluble salt by condensation of hydrazine hydrate with cyanamide in the presence of an inorganic acid, usually sulfuric acid, and isolated in the form of a poorly soluble bicarbonate by carbonation in an alkaline medium, as shown in French Pat. No. 1,241,151.

This prior art commercial process, however, has major disadvantages. The economics are adversely affected by a number of factors. First, a large excess of cyanamide is required to obtain complete conversion of the hydrazine hydrate; an inorganic acid is used and this accordingly requires an alkaline agent in the carbonation stage. Further, it entails consumption of carbon dioxide; loses yield due to partial solubility of the aminoguanidine bicarbonate in the mother liquors and washes, recycling of which is impossible, particularly because of the presence of inorganic ions; and occasions a large volume of heavy polluting effluents which it is impossible to purify to an acceptable level.

Additionally, 3-amino-1,2,4-triazole from this prior art process is insufficiently pure. The aqueous solutions are not easily filterable, an indication of the presence of insoluble products which, while present in small amounts, are all the more difficult because in most cases they are in the form of a gel.

Published Japanese patent application No. 72/08,820 suggests preparing 3-amino-1,2,4-triazole by the reaction of hydrazine hydrate with cyanamide in the presence of formic acid, this operation being carried out in a single stage (Examples 1 to 9) or in two stages (Example 10). In both cases, the purity of the 3-amino-1,2,4-triazole produced is unsatisfactory, because the aqueous solutions develop more or less gelatinous flocculates, which are difficult to remove. Furthermore, the yield obtained by operating as in Example 10 is too low to make this process economically viable.

THE INVENTION

A process which makes it possible to obtain a high yield of 3-amino-1,2,4-triazole with excellent purity, that is, absence of flocculate in aqueous solutions, from hydrazine hydrate, cyanamide and formic acid has now been discovered.

The process according to this invention comprises first reacting hydrazine hydrate, cyanamide and formic acid, and then separately cyclizing the aminoguanidine formate so produced wherein (a) hydrazine hydrate and formic acid are simultaneously added to the cyanamide to maintain the temperature from 0° C. to 10° C., preferably between 0° and 5° C., while controlling the pH (measured at 4° C.) at from 6 to 7, and preferably between 6.3 and 6.5;

(b) the mixture is then heated to a temperature of from 60° to 100° C., preferably between 75° and 85° C., and maintained there until the disappearance of hydrazine hydrate, the pH (measured at 20° C.) being maintained between 7 and 8, preferably between 7.5 and 7.7, by addition of formic acid;

(c) the aminoguanidine formate solution thus obtained is then partially evaporated at a temperature of from 30° to 60° C., preferably between 35° and 45° C. until the solids content is between 100 and 700 g/L and preferably in the region of 500 g/L;

(d) the suspension is filtered and the crystallized aminoguanidine formate is washed until its dicyandiamide content is below 0.25% with respect to the weight of dry formate, the mother liquors and a part or all of the washes being recycled to the evaporation; and (e) the aminoguanidine formate is heated at a temperature of between 110° and 200° C., preferably between 140° and 170° C.

The concentrations of the three starting materials can be varied without greatly affecting the process. In certain embodiments, it is preferred to use pure hydrazine hydrate or aqueous solutions thereof with a concentration above 35% by weight. It is also preferred to use pure formic acid or aqueous solutions with a concentration above 70% formic acid by weight. The cyanamide in certain embodiments is preferably employed in the form of aqueous solutions with concentrations of from 100 to 250 g/L. While, as noted above, various concentrations are useful in practicing the present invention, lower concentrations result in a water-diluted medium, giving rise to an unfavorable heat balance during evaporation. Higher concentrations have an unfavorable effect on the washing phase. The cyanamide can also be used in solutions in an organic solvent, for example, an alcohol such as butanol.

Although the molar relationship of the three reactants can be stoichiometric, (one mole of cyanamide and one mole of formic acid per mole of hydrazine), it is desirable, in order to improve the reaction rate, to use a molar excess of cyanamide of from 0 to five percent, with respect to the hydrazine. In certain preferred embodiments, the molar excess of hydrazine is from 0 to three percent. Similarly, a molar excess of formic acid from 0 to eight percent is desirable with between two and six percent used in preferred embodiments.

The evaporation is desirably carried out under a vacuum of from 10 to 100 torr, and in preferred embodiments between 20 and 30 torr. This evaporation and the subsequent filtration and washing steps are preferably carried out continuously. After a period to attain steady-state operation during which, as a result of recycling of the mother liquors and a part or all of the washes, the content of impurities is allowed to rise to a value corresponding to a dicyandiamide concentration of between 5 and 15%, preferably between 8 and 12%, the system is purged by withdrawing from the mother liquors a quantity of liquid such that a quantity of impurities removed is equivalent to that of the formate solution delivered to the evaporator. The aminoguanidine formate entrained by this purge can be recovered and used separately for the manufacture of 3-amino-1,2,4-triazole of lower purity than that aimed at by the present invention.

All parts, percentages, proportions, and ratios herein are by weight, unless otherwise stated.

The following Example is given to illustrate embodiments of the invention as it is presently preferred to practice it. It will be understood that this Example is illustrative, and the invention is not to be considered as restricted thereto except as indicated in the appended claims.

EXAMPLE

A reactor fitted with an agitator, a pH monitor to control formic acid addition, a temperature probe, and a liquid-cooled heat exchanger is charged with 31,330 liters of an aqueous solution of cyanamide at a concentration of 160 g/L and 3 kg of the disodium salt of ethylenediaminetetraacetic acid complexing agent with stirring and under a nitrogen blanket. After cooling to +3° C. to +4° C., 7,100 liters of an 80% hydrazine hydrate solution is added with stirring and without exceeding a temperature of +4° C. This addition is carried out while the pH (measured at +4° C.) is maintained at 6–6.5 by simultaneous addition of 4,549 liters of 100% formic acid.

The solution so obtained is transferred to a reactor equipped with an agitator, stirring, temperature sensor, pH sensor in the reaction recycle solution cooled at +20° C., a nitrogen inlet, and a heat exchanger system to permit heating the solution to 80° C. and controlling the exotherm produced at about 70° C. by cooling during the temperature rise. The temperature of the solution is raised to 80° C. and is maintained until the concentration of hydrazine hydrate is below 1 g/L. During this time the pH, measured at 20° C., is maintained at 7.6 by adding 120 liters of 100% formic acid. The solution of aminoguanidine formate so produced is then transferred to a buffer tank kept under a nitrogen blanket. It has a volume of 40,900 liters, or 44,755 kg by weight.

An evaporator is fed continuously from the buffer tank with 1,705 L/hr of aminoguanidine formate solution and 1,585 L/hr of the mother liquors and the first and second wash liquors originating from a previous filtration of aminoguanidine formate. The evaporation of this mixture is carried out at approximately 35° C. under a vacuum of 20 to 30 torr. The suspension obtained at the outlet of the evaporator has a solids concentration in the region of 500 g/L and is transferred to a crystallizer maintained at 20° C.

The suspension (2,185 kg/hr) is then filtered, and then the solid is washed thrice. It is first washed with 150 kg/hr of liquor originating from the third washing, then with 180 kg/hr of purified water, and finally with 75 kg/hr of purified water.

An output of 573 kg/hr of aminoguanidine formate containing 5% of water is obtained. The mother liquors and the liquors produced in the first and second washing are recycled to the evaporator, while the liquors produced in the third washing are employed in the first washing.

A glass-lined reactor fitted with stirrer, temperature sensor, vacuum line, and heat exchanger capable of heating to 160° C. is charged with 2,749 kg of aminoguanidine formate containing 5% of water, obtained above. At atmospheric pressure, the contents are heated to 120° C., a temperature at which melting of the formate takes place. The temperature of the mixture is then raised to 155°–160° C. over approximately one and a half hours under a vacuum of 20 to 30 torr. The reactor is returned to atmospheric pressure and the temperature maintained at 155°–160° C. for an hour and a half. The product is then transferred to a flaker.

In this way 1,800 kg of 3-amino-1,2,4-triazole is produced, with the following characteristics:
Purity: 97–98%
Water content: 0.15%
Filterability: 5–10 seconds
Insoluble flocculate: None.

To assess filterability, 30 g of 3-amino-1,2,4-triazole are dissolved in 70 ml of water at 35° C., and then filtration is carried out under a vacuum of 60 torr through a glass fiber filter (Whatman G F/C) 70 mm in diameter.

What is claimed is:

1. A process for the preparation of 3-amino-1,2,4-triazole which comprises simultaneously adding hydrazine hydrate and formic acid to cyanamide at a temperature of from 0° to 10° C. and a pH (measured at 4° C.) of 6 to 7; bringing the mixture so formed to a temperature of 60° to 100° C. at a pH (measured at 20° C.) of 7 to 8 and maintaining the mixture at such temperature and pH, until substantially no hydrazine hydrate remains, to obtain aminoguanidine formate; evaporating liquid from the aminoguanidine formate solution at a temperature of from 30° to 60° C. to obtain a suspension having a solids content of from 100 to 700 g/L; filtering the suspension obtained to remove the solids from suspension in the mother liquor; washing the solids so obtained with a wash medium to produce a dicyandiamide content of less than 0.25 percent by weight, based on the dry formate; withdrawing the wash medium from the solids; and heating the washed solids so obtained to a temperature of from 110° to 200° C. to cyclize the formate and produce the aminotriazole.

2. A process according to claim 1 wherein at least a portion of the mother liquor from the filtration and of the wash medium is recycled to the evaporation.

3. A process according to claim 2 wherein all of the mother liquor is recycled.

4. A process according to claim 1 wherein the evaporation is carried out under vacuum at a temperature of from 35° to 45° C. to obtain a solids content of about 500 g/L.

5. A process according to claim 4 wherein the vacuum is from 10 to 100 torr.

6. A process according to claim 1 wherein the mole ratio of hydrazine/cyanamide/formic acid is from 1/1/1 to 1/1.05/1.08.

7. A process according to claim 1 wherein the addition of the hydrazine hydrate and formic acid is carried out at 0° to 5° C. and a pH of 6.3 to 6.5.

8. A process according to claim 1 wherein the mixture so formed is kept at 75° to 85° C. and a pH of 7.5 to 7.8.

9. A process according to claim 1 wherein the evaporation is carried out at from 35° to 45° C.

10. A process according to claim 1 wherein the cyclization heating is carried out at 140° to 170° C.

* * * * *